United States Patent [19]

Chiang

[11] 4,439,595
[45] Mar. 27, 1984

[54] CHLORINATION OF HYDROQUINONE

[75] Inventor: Chih S. Chiang, Wilmington, Del.

[73] Assignee: E. I. Du Pont de Nemours & Company, Wilmington, Del.

[21] Appl. No.: 477,586

[22] Filed: Mar. 21, 1983

[51] Int. Cl.$^3$ .................. C07C 39/24; C08G 63/68
[52] U.S. Cl. .................................. 528/191; 528/193; 528/194; 568/765; 568/774; 568/779
[58] Field of Search ............... 528/765, 191, 193, 194; 568/726, 774, 776–779

[56] References Cited

U.S. PATENT DOCUMENTS

| 2,748,173 | 5/1956 | Rodgers | 260/623 |
| 4,075,119 | 2/1978 | Schmidt et al. | 252/182 |
| 4,210,765 | 7/1980 | Mark | 568/726 |

OTHER PUBLICATIONS

Masilamani and Rogic, J. Org. Chem. 1981, 46, pp. 4486–4489.

*Primary Examiner*—Lester L. Lee

[57] ABSTRACT

Chlorination of hydroquinone by reacting sulfuryl chloride with hydroquinone in an alkyl ester solvent having 2–8 carbon atoms yields a mixture containing a major proportion of monochlorohydroquinone.

6 Claims, No Drawings

CHLORINATION OF HYDROQUINONE

BACKGROUND OF THE INVENTION

1. Field of the Invention

This invention relates to a new process for chlorinating hydroquinone in an alkyl ester solvent for coupled acetylation and polymerization with appropriate comonomers to give melt-spinnable anisotropic-melt-forming copolyesters.

2. Description of the Prior Art

U.S. Pat. No. 2,748,173 discloses the reaction of hydroquinone with chlorine in aqueous acetic acid at elevated temperatures to obtain a mixture of hydroquinone and chlorinated hydroquinones.

A statistical mixture of halogenated and non-halogenated bisphenols are said to be obtained by reaction of chlorine and/or bromine with a suspension of a bisphenol in an inert gas or a halogenated hydrocarbon according to U.S. Pat. No. 4,075,119. An improvement over the use of elemental chlorine is said to be achieved by reacting bisphenols with sulfuryl chloride in methylene chloride or benzene according to U.S. Pat. No. 4,210,765.

Masilamani and Rogic, J. Org. Chem., 46, pp. 4486-4489 describe the reaction of phenol with sulfuryl chloride in methylene chloride plus a selected organic "base" to yield a mixture of chlorinated phenols. Reaction of sulfuryl chloride with a bisphenol in ether is also reported in this article.

SUMMARY OF THE INVENTION

One aspect of the present invention is directed to a process for chlorinating hydroquinone to obtain a chlorinated mixture comprising a major proportion of monochlorohydroquinone. This process comprises adding sulfuryl chloride to a slurry or solution of hydroquinone and an alkyl ester having 2-8 and preferably 2-4 carbon atoms as a solvent, the mole ratio of sulfuryl chloride to hydroquinone being in the range of from about 0.55 to about 1.2. The esters and by-product hydrogen chloride and sulfur dioxide are removed by volatilization. In another aspect of the invention, the resulting chlorinated mixture is acetylated by heating with acetic anhydride to provide an acetylated chlorinated hydroquinone mixture. Appropriate monomers may then be combined and polymerized with the acetylated chlorinated hydroquinone mixture to yield melt-spinnable anisotropic-melt-forming polyesters.

DETAILED DESCRIPTION OF THE INVENTION

The chlorination process of the present invention has a number of advantages. Chlorohydroquinone, i.e. the monochlorohydroquinone, is a desirable monomer for the production of anisotropic-melt-forming polyester (see U.S. Pat. Nos. 4,118,372 and 4,347,349). The present process produces high yields of a mixture having a major proportion, generally in excess of about 50 mol % of chlorohydroquinone. The other components of the chlorinated mixture are principally unreacted hydroquinone and dichlorohydroquinones, all of which are compatible with the subsequent acetylation and polymerization reactions. The instant chlorination process produces no significant quantities of undefined by-products which interfere with subsequent use of the chlorinated mixture in the production of copolyesters as by imparting coloration or causing cross-linking of the polyester with loss of melt-spinnability. The volatile by-products of the chlorination, namely, HCl and $SO_2$, are readily swept from the reaction vessel along with the ester solvent. The chlorinated mixture can therefore be used directly, without purification for the production of polyesters, particularly, anisotropic-melt-forming polyesters. Of course, if pure chlorohydroquinone is desired one can isolate it in pure form by distillation. The chlorinated mixture may be directly acetylated with acetic anhydride for use in polymerization reactions with other monomers. If the acetylated chlorinated mixture is to be used in polymerization, the acetic acid by-product and excess acetic anhydride may be removed either before or after addition of other monomers.

It has been found that the properties of polyester yarns and moldings prepared from the acetylated chlorinated hydroquinone mixtures resulting from this invention are not significantly different from those made from purified chlorohydroquinone. The chlorination conditions selected for the present process may influence yield of the desired chlorohydroquinone to a great extent. Maximum yields of chlorohydroquinone are obtained using a mole ratio of sulfuryl chloride to hydroquinone in the range of about 0.55-1.2, preferably 0.65-0.90. It is preferred that the above range not be exceeded by any significant amount to minimize the amount of overreacted and unreacted material.

The reaction can be carried out in slurry but preferably is carried out with a solution of hydroquinone in the alkyl ester. Examples of operable esters having 2-8 and preferably 2-4 carbon atoms include methyl formate, acetate, propionate, butyrate, valerate, hexanoate, heptanoate; ethyl formate, acetate, propionate, butyrate, valerate, hexanoate; n- and isopropyl formate, acetate, propionate, butyrate; n- and isobutyl formate, acetate, propionate, butyrate; pentyl formate, acetate, propionate; hexyl formate, acetate; and heptyl formate. Ethyl acetate is preferred.

The reaction can be conducted at or about room temperature but preferably is conducted at a temperature in the range of about 5°-20° C. Preferably the sulfuryl chloride is added gradually with agitation to assure its rapid and uniform distribution.

The chlorinated hydroquinone mixture is next acetylated by refluxing with excess acetic anhydride. This reaction releases acetic acid which may be recovered along with any excess acetic anhydride.

Comonomers such as terephthalic acid may be added either before or after removal of the excess acetic anhydride and the acetic acid. In either case removal is achieved by distillation before full polymerization is achieved. The succeeding steps in melt polymerization follow normal procedures.

The resulting polymer may be melt spun into fiber or if desired, melt-extruded into bars or molded into shaped articles. Physical properties were determined as follows:

Monofilament tensile properties were measured using a recording stress-strain analyzer at 70° F. (21.1° C.) and 65% relative humidity. Gauge length was 1.0 in (2.54 cm), and rate of elongation was 10%/min. Results are reported as T/E/M where D is linear density in tex units, T is break tenacity in dN/tex, E is elongation-at-break expressed as the percentage by which initial length increased, and M is initial tensile modulus in dN/tex. Average tensile properties for three to five filament samples are reported.

The examples which follow illustrate various aspects of the present invention but are not intended to limit the invention in any respect.

EXAMPLE 1

This Example shows preparation of a mixture of chlorinated hydroquinones which can be used directly in melt polymerization.

In a standard 1 liter 3 neck flask, equipped with an addition funnel, a reflux condenser, and a thermometer, immersed in an ice bath, was placed 110 g (1.0 mole) of hydroquinone, 400 ml of ethyl acetate, and an egg shaped spin bar. To this solution under nitrogen was added dropwise 140 g (1.1 mole) of $SO_2Cl_2$ during a period of one hour. Temperature of the reaction mixture was kept between 5° C. to 20° C. during the addition. Upon complete addition, the reaction temperature was raised to 60° C. by gentle heating for ½ hour to ensure complete $SO_2$ and HCl removal. The resulting solution was evaporated on a rotary evaporator to remove ethyl acetate. A viscous liquid was obtained (155.8 g) which rapidly solidified on standing at room temperature. Gas chromatographic analysis of this solid showed it contained 9.0% hydroquinone, 78% chlorohydroquinone, and 12.1% dichlorohydroquinone. A portion of this mixture (36.4 g) was charged to a glass flask along with 11.72 g (0.063 mole), of 4,4'-dihydroxybiphenyl, 39.84 g (0.24 mole) terephthalic acid and 9.96 g (0.06 mole) isophthalic acid was added. The flask was evacuated and purged three times with argon whereupon 0.07 g of sodium acetate and 70 ml of acetic anhydride were added. The reaction mixture was heated by immersing slowly in a Wood's metal bath and stirred with a continuous argon purge at an initial bath temperature of 260° C. which was increased slowly to 339° C. in 52 minutes while continually removing acetic acid and acetic anhydride. The pressure then was slowly reduced to 2.5 mm Hg and then to about 0.8 mm Hg in the next 2 minutes while the bath temperature was maintained at 335°–340° C. at which time the argon flow was stopped. The flask was cooled; the polymer isolated. Yield was 73.8 g, 87%. Fibers could be pulled from the melt at 323° C.

A molded plug of the polymer was melt spun through a 0.23 mm orifice and a bobbin of 10 filament yarn was collected at 500 m/min when the spinneret temperature was at 318° C. The yarn was heat treated in a relaxed state in an oven purged with nitrogen by heating from room temperature to 200° C. in 3 hours; 200°–305° C. in 6½ hours and held at 385° C. for 8½ hours then permitted to cool to room temperature under the nitrogen purge. Table 1 shows the properties of the filaments before and after heat treatment.

TABLE 1

| Fiber | Tenacity T (dN/tex) | Elongation E (%) | Modulus $M_i$ (dN/tex) | tex* |
|---|---|---|---|---|
| As-spun | 4.2 | 1.2 | 439 | 6.2 |
| Heat treated | 14.2 | 2.8 | 483 | 6.0 |

*tex = $0.785 \times 10^{-3}$ (dia, μm)$^2$ g/cm$^3$, linear density of fiber

EXAMPLE 2

Example 1 was repeated except that 108 grams (0.8 mole) of $SO_2Cl_2$ were added and 164.2 grams of viscous liquid product containing 27.8% unreacted hydroquinone, 66.4% monochlorohydroquinone and 5.6% dichlorohydroquinone was obtained. Polymer prepared from the product according to the general procedure of Example 1 exhibits satisfactory physical properties.

I claim:

1. A process for chlorinating hydroquinone to obtain a chlorinated mixture comprising a major proportion of monochlorohydroquinone which process comprises adding sulfuryl chloride to a slurry or solution of hydroquinone and an alkyl ester having 2–8 carbon atoms, the mole ratio of sulfuryl chloride to hydroquinone being maintained in the range of from about 0.55 to about 1.2.

2. The process of claim 1 wherein 0.65–0.90 mole of sulfuryl chloride is present per mole of hydroquinone.

3. The process of claim 2 wherein the alkyl ester has 2–4 carbon atoms.

4. The process of claim 2 wherein the alkyl ester is ethyl acetate.

5. A process for preparing a melt-spinnable anisotropic-melt forming polyester by reacting chlorohydroquinone with other monomers comprising 4,4'-dihydroxybiphenyl, terephthalic acid and isophthalic acid which process comprises adding sulfuryl chloride to a slurry or solution of hydroquinone and an alkyl ester having 2–8 carbon atoms, the mole ratio of sulfuryl chloride to hydroquinone being in the range of from about 0.55 to about 1.2 to obtain a chlorinated mixture, acetylating the mixture by heating with acetic anhydride, adding said other monomers and polymerizing the mixture.

6. The process of claim 1 wherein the product is acetylated and polymerized without purification.

* * * * *